US00RE37903E

(19) United States
(12) Reissued Patent
Riskin

(10) Patent Number: US RE37,903 E
(45) Date of Reissued Patent: Nov. 12, 2002

(54) MEDICATION APPLICATOR WITH INCIDENT REMINDER SYSTEM

(76) Inventor: Jane G. Riskin, 217 Ruth Ave., Venice, CA (US) 90291

(21) Appl. No.: 09/773,875

(22) Filed: Feb. 2, 2001

Related U.S. Patent Documents

Reissue of:
(64) Patent No.: 6,092,692
Issued: Jul. 25, 2000
Appl. No.: 09/307,861
Filed: May 10, 1999

(51) Int. Cl.[7] ..... B67D 5/06
(52) U.S. Cl. ..... 222/23; 222/182; 222/321.6
(58) Field of Search ..... 222/23, 47, 48, 222/321.2, 321.6, 321.7, 321.9, 182; 128/200.18, 200.14, 200.22; 604/514, 94, 73

(56) References Cited

U.S. PATENT DOCUMENTS 4,801,093 A * 1/1989 Brunet et al. ..... 604/94
5,431,155 A * 7/1995 Marelli ..... 128/200.14
5,433,191 A * 7/1995 Haber et al. ..... 128/200.14

* cited by examiner

*Primary Examiner*—Henry C. Yuen
*Assistant Examiner*—Thach H. Bui
(74) *Attorney, Agent, or Firm*—Jack C. Munro

(57) ABSTRACT

A medication dispensing applicator which utilizes indicia inscribed on different parts of the applicator to inform a user which nostril or other body location was last utilized in dispensing of the medication and when the medication was dispensed. This information is to inform the user when and where the medication was last dispensed so the user can readily determine what is the correct time for a further dispensing of medication and as to which location the medication is to be dispensed as locations are to be alternated.

6 Claims, 2 Drawing Sheets

MEDICATION APPLICATOR WITH INCIDENT REMINDER SYSTEM

Matter enclosed in heavy brackets [ ] appears in the original patent but forms no part of this reissue specification; matter printed in italics indicates the additions made by reissue.

BACKGROUND OF THE INVENTION

1) Field of the Invention

The field of this invention relates to medication dispensers and more particularly to a liquid medication applicator that is to be used to dispense liquid medication within the nasal passages or between any two spaced apart locations of a human or other animal body.

2) Description of the Prior Art

Nasal medication applicators have long been known. A common form of such an applicator utilizes a vessel within which contains a quantity of liquid medication. Medications include prescription drugs, natural medicines and vitamin solutions. The vessel is closed by a cap. Mounted on the cap is an injector nozzle with this injector nozzle having a wing structure which includes a pair of wing members that are diametrically located opposite the injector nozzle which is basically of cylindrical construction. The user is to grasp the vessel and place a finger on each wing member and move the injector nozzle toward the vessel. This will cause a precise quantity of the liquid medication to be dispensed through a dispensing opening formed within the injector nozzle. When the applicator is not being used, a cover can be removably attached to the injector nozzle closing the dispensing opening relative to the ambient. It is the function of the cover to prevent contamination of the dispensing opening by foreign matter from the ambient. The cover is to be removed from the injector nozzle prior to utilizing of the applicator.

Some medications are best dispensed within the human body by utilizing the nasal passages. A precise quantity of the medication is to be dispensed by an applicator into either the right nostril or the left nostril of the nose of the user. It is common for this medication to be dispensed once a day. When it is preferable to minimize the possible damage to the nasal passages, the right nostril is utilized one day and the left nostril is utilized the second day with the right nostril then being reutilized the third day, and so forth. However, when the user picks up the applicator to dispense the medication, the user invariably cannot remember which nostril was last used. Also, the user might have trouble remembering whether the applicator was last used the day before and that possibly that day could have been missed. There is a need to incorporate in conjunction with the nasal medication dispensing applicator a day reminder system and a nostril reminder system so that when the user picks up the applicator to use it that user can quickly ascertain when the applicator was last used and with which nostril the applicator was last used.

SUMMARY OF THE INVENTION

A nasal medication dispensing applicator which has a cap which closes the access opening of a vessel within which is a reservoir that contains a quantity of a liquid medication. Mounted on the cap is an injector nozzle that is freely pivotally movable on the cap and also is movable lineally toward and away from the cap. The injector nozzle includes a wing structure that is formed into a pair of wing members. A cover is connectable with the injector nozzle. Nostril last sprayed indicia is inscribed on the cap with one wing member having a left indicating nostril indicia and the opposite wing member having a right indicating nostril indicia. If the left indicating nostril indicia is aligned with the nostril last sprayed, the user is informed that the left nostril of the user's nose was last sprayed with the applicator. If the right indicating nostril indicia is aligned with the nostril last sprayed indicia, then the user knows that the right nostril was the last sprayed. A cover is movably attachable to the injector nozzle with a cover including indicia representing the days of the week. When a particular day of the week is aligned with the nostril last sprayed, the user is informed which day of the week the applicator was last used.

DETAILED DESCRIPTION OF THE PREFERRED EMBODIMENT

Figure 3:
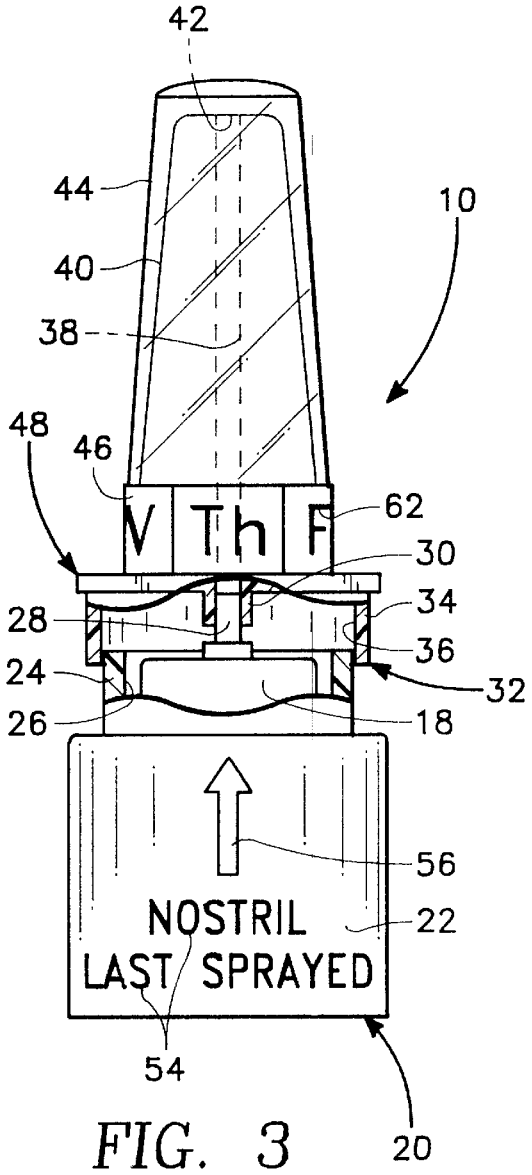
FIG. 3 is a view, partly in cross-section, of the cap of the nasal medication dispensing applicator of the present invention.

Referring particularly to the drawings, there is shown the nasal medication applicator 10 of this invention. The dispensing applicator 10 of this invention includes a vessel 12 which contains a reservoir within which is located a quantity of a liquid medication 14. A tube 16 extends within the reservoir and is submerged within the liquid medication 14. The tube 16 connects with a pump 18 which is fixedly mounted within a cap 20. The cap 30 includes a main section 22 which is basically of cylindrical configuration with this main section 22 to be threadably mounted onto the vessel 12. The cap 20 also includes a smaller diameter top section 24 which includes an internal through opening 26. The pump 18 is mounted within the opening 26. The pump 18 includes a dispensing tube 28 with this dispensing tube 28 being mounted within a sleeve 30 of an injector nozzle 32. The injector nozzle 32 includes a cylindrically shaped base section 34 which is basically hollow forming internal compartment 36. The top section 24 is to be locatable in a close fitting manner within the internal compartment 36. The base section 34 is to be lineally movable from the position shown in FIG. 3 toward the main section 22. A spring, which is not shown, is to be included between the base section 34 and the top section 24 exerting a continuous bias tending to locate the applicator 10 shown in the position in FIG. 3. When the base section 34 has been moved lineally relative to the main section 22, once this movement has been completed and the force of the movement is released, the base section 34 will then automatically move back to the position shown in FIG. 3.

Downward movement of the base section 34 toward the main section 22 will cause a small amount of medication 14 to be conducted up the tube 16 through the dispensing tube 28 into the dispensing passage 38. The dispensing passage 38 is formed within elongated nozzle section 40 of the injector nozzle 32. The upper end of the dispensing passage 38 terminates in a dispensing opening 42. From the dispensing opening 42, a precise quantity of the medicine is to be dispensed into the ambient by the movement of the base section 34 in a direction toward the main section 22 or toward the vessel 12.

Figure 1:
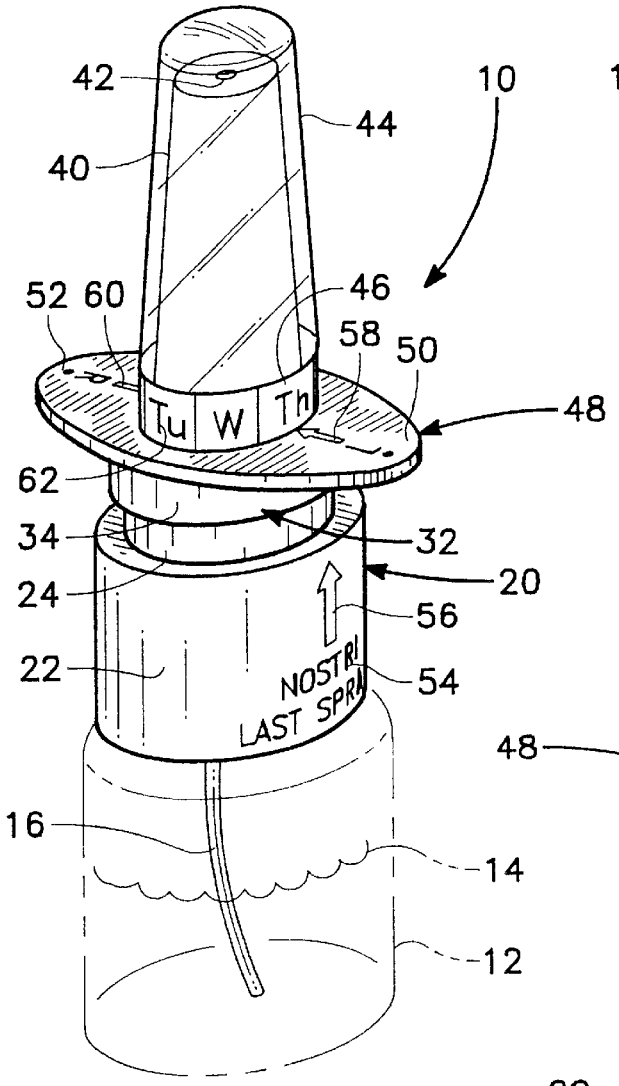
FIG. 1 is an isometric view of the nasal medication dispensing applicator of the present invention showing the applicator in the non-usage position indicating that the left nostril was last sprayed on Thursday of the week.
Figure 2:
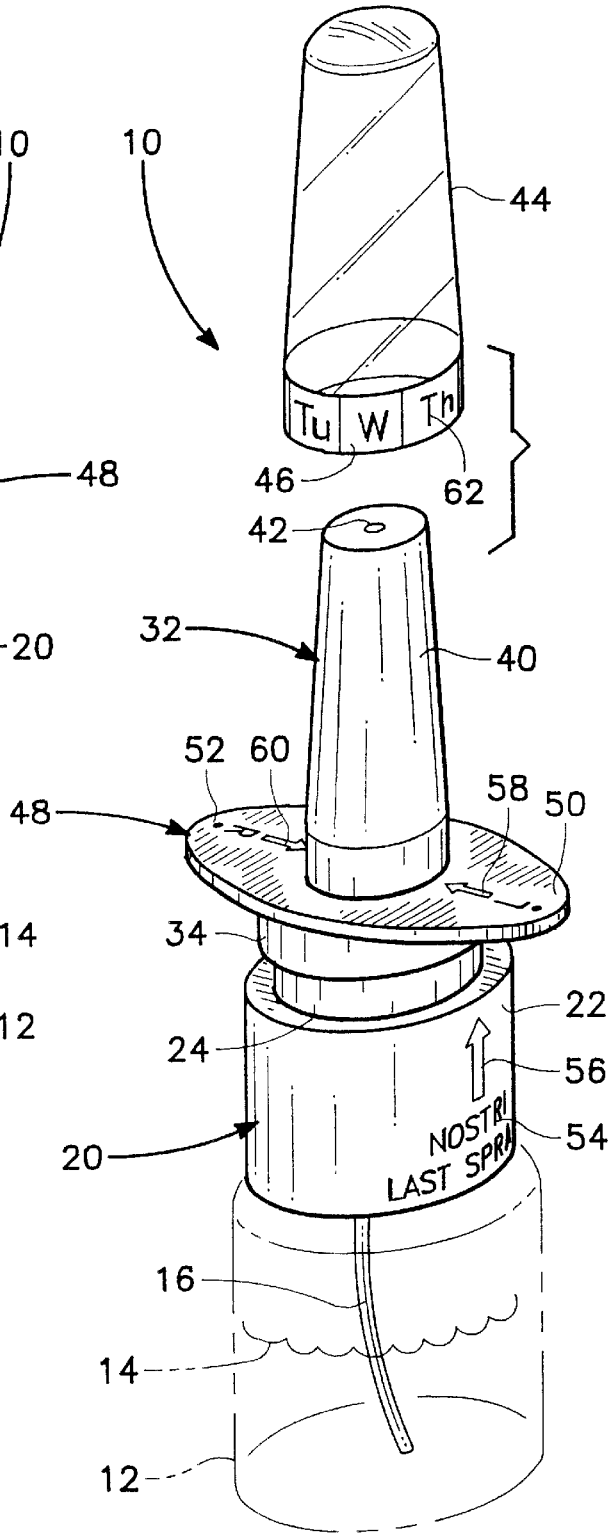
FIG. 2 is an isometric view of the nasal medication dispensing applicator of the present invention showing the cover of the applicator disengaged from the injector nozzle permitting the applicator to then be used.

When the applicator 10 is not being used, a cover 44, generally transparent, is located about the nozzle section 40. The base portion 46 of the cover 44 is located in abutting contact with the wing structure 48 of the injector nozzle 32. Actually, the cover 44 will be snugly held in the position shown in FIGS. 1, 3 and 4, but the cover 44 can be easily removed from the injector nozzle 32 as is shown in FIG. 2 of the drawings.

The wing structure 48 includes wing members 50 and 52. The wing structure 48 is basically planer with the wing members 50 and 52 extending outwardly from the nozzle section 40 with wing member 50 being located diametrically opposite wing member 52. The user is to place one finger, such as a forefinger, on top of wing member 50 with the middle finger being located on top of wing member 52. The user's thumb is to be located underneath the vessel 12. By manually pushing against the wing structure 48 by the fingers will cause the injector nozzle 32 to be moved relative to the top section 24 resulting in a precise quantity of the medicine 14 to be dispensed through the dispensing passage 38 and then ejected in mist form from the dispensing opening 42.

Inscribed on the main section is first indicia 54. The first indicia 54 can include the words such as "nostril last sprayed" and an arrow 56 with this arrow 56 pointing upward toward the top section 24. On the upper surface of wing member 50 is located the letter "L" and an arrow 58. In a similar manner, on the upper surface of wing member 52 is located the letter "R" and an arrow 60. Both arrows 58 and 60 point directly toward the nozzle section 40 and are in alignment with each other. Actually, arrow 58 is located diametrically opposite the arrow 60.

On the base portion 46 of the cover 44 there is inscribed second indicia 62 in the form of the days of the week. Actually, the indicia 62 is divided into seven equal sized areas and within each area is located an indicia such as "M" for Monday, "T" for Tuesday, "W" for Wednesday, "TH" for Thursday, "F" for Friday, "SA" for Saturday and "SU" for Sunday.

The operation of the applicator 10 of this invention is as follows: When the user picks up the applicator 10, the user notes which wing member 50 or 52 is in alignment with the arrow 56. If it happens to be as shown in FIG. 1, the wing member 50 is in alignment with the arrow 56 which indicates to the user that the left nostril, because the letter "L" is inscribed on the upper surface of the wing member 50, was last sprayed, usually the day before. The user also notices arrow 58 which clearly points to indicia 62 and specifically the "TH" of indicia 62 to inform the user that the applicator 10 was last used on Thursday. The user then removes cover 44 and places his or her fingers on the wing structure 48, as previously described, and causes the applicator to dispense a quantity of the liquid medication from the dispensing opening 42. Prior to this, the user should have placed the nozzle section 40 within the right nostril of the user since the left nostril was indicated as being used at the last application.

Figure 4:
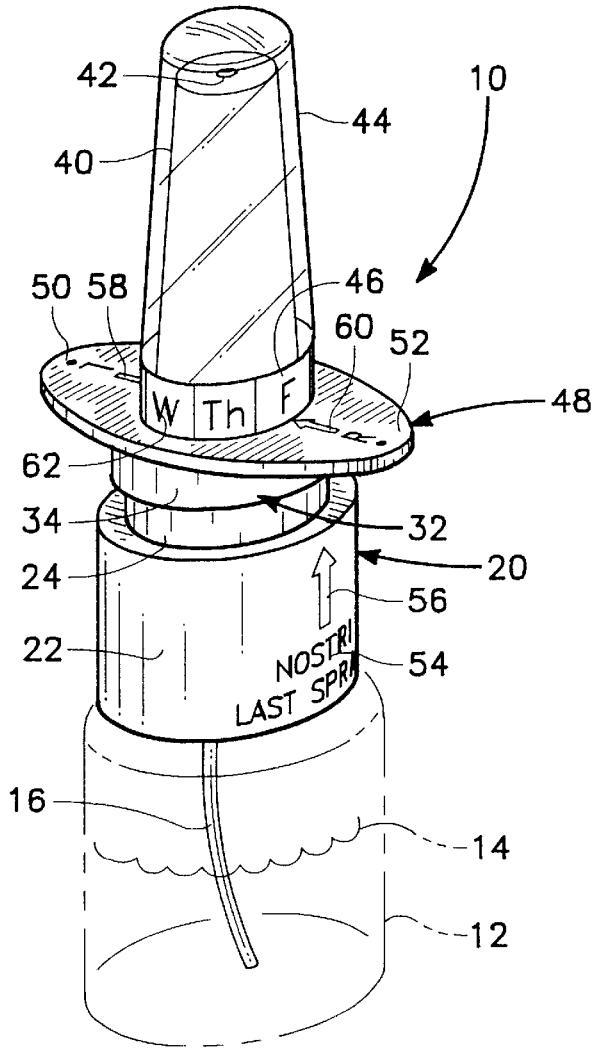
FIG. 4 is an isometric view similar to FIG. 2 where the nostril last sprayed is shown to be the right nostril with the day of the week of the application being noted as Friday.

After the dispensing of the precise quantity of medication 14, the nozzle section 40 is removed from the right nostril and then the user pivots the wing structure 48 so that the wing member 52 and the letter "R" aligns with arrow 56, as is clearly shown in FIG. 4 of the drawings. The user then replaces the cover 44 over the nozzle section 40 until the base 46 again abuts against the wing structure 48. Actually, there will probably be some form of a slight detent arrangement between the cover 44 and the nozzle section 40 so that the cover 44 will "snappingly engage" when the nozzle section 40 is in the installed position against the wing structure 48. The user then pivots the cover 44 until the letter "F" aligns with arrow 52. This now means that the right nostril was just sprayed and it was sprayed on Friday. The applicator 10 is then put away in its appropriate storage location. Now when the user picks up the applicator 10 again to be reused, which should be the next succeeding day, the user can readily determine from the applicator that the nostril layer sprayed was the right nostril and it was sprayed on Friday. Reuse of the applicator is to occur as previously mentioned, and after usage the wing structure is then pivoted Bo now the letter "L" of wing member 50 aligns with arrow 56, and when the cover 44 is replaced on the nozzle section 40, the letters "SA" (not shown) for Saturday, is to be aligned with arrow 58. It is to be understood that this operating arrangement is to be continued for each succeeding day and after each application.

Although the present invention has been described in relation to a left nostril and a right nostril and application of a medication within one nostril one day and the other nostril the next day, it is considered to be within the scope of this invention that other applications might be possible. For example, the second indicia may not reference the day of the week but instead could comprise only two segments including in the AM and PM or include a plurality of segments denoting such as four times a day. Possibly, also the first indicia could comprise reference to AM and PM and the second indicia could reference the days of the week. Possibly, there are multiple numbers of alternatives in which the first indicia and second indicia could be utilized as a reminder system for the taking of medication by a human or other animal which falls within the scope of this invention which is not even apparent to the applicant at this time. Medication is meant to include prescription drugs, non-prescription drugs, creams, sprays or injections.

It is considered to be within the scope of this invention that this invention could be used in any application that requires a pair of separate application locations. Also, the application could be used to inject a substance under the skin, could be to apply a cream, could be to apply a spray, et cetera.

What is claimed is:

1. A [nasal medication] *substance* applicator with incident reminder system [usable in conjunction with a nose having a left nostril and a right nostril] comprising:

a vessel having an internal reservoir adapted to contain a quantity of a [liquid medication] *substance*;

a [cap] *pump* mounted on said vessel, [said cap including a pump,] said pump being actuatable to dispense the [liquid medication] *substance*, said [cap] *vessel* having *a* first indicia, said first indicia indicating [which nostril of the left nostril and the right nostril was last sprayed with the liquid medication] *the time of alternative times or the location of alternative locations of application of the substance*; and an injector nozzle mounted on said [cap] *vessel*, said injector nozzle being movable relative to said [cap] *vessel* between a dispensing position and a non-dispensing position, [said injector nozzle also being freely pivotally movable on said cap,] said injector nozzle having a wing structure [forming a pair of diametrically spaced apart wing members], applying a downward force toward said vessel against said wing [members] *structure* results in movement of said injector nozzle from said non-dispensing position to said dispensing position with some of the [liquid medication] *substance* to be ejected from said injector nozzle [in the form of a misting spray], [left] *second* indicating indicia located on [one] said wing [member] *structure*, [right] *third* indicating indicia *also* located on [the remaining] said wing [member] *structure*, with said [left] *second* indicating indicia being aligned with said first indicia the user is informed [that the left nostril was last sprayed] *of a time or location of application*, with the [right] *third* indicating indicia being aligned with said first indicia the user is informed [that the right nostril was last sprayed] *of an alternative time or location of application*.

2. The [nasal medication] *substance* applicator as defined in claim 1 including:

a cover removably connectable with said injector nozzle, said cover being pivotable relative to said injector nozzle, said cover having [second] *fourth* indicia referencing each day of the week, a selected day of the week of said [second] *fourth* indicia to be aligned with [either] said [left] *second* indicating indicia or said [right] *third* indicating indicia that is aligned with said first indicia thereby informing the user [which day of the week the nasal medication applicator was last used] *of the day of the week of application of the substance*.

3. The method of applying liquid medication in a spray within either a left nostril or a right nostril of a nose comprising the steps of;

utilizing an applicator that has a liquid method containing vessel on which is mounted a cap upon which is noted first indicia indicating which nostril (either left or right) was last sprayed with said applicator;

utilizing an applicator that has an injector nozzle mounted on said cap which is pivotally movable and lineally movable relative to said cap;

utilizing a wing structure on said injector nozzle that has a pair of diametrically spaced apart wing members with one of said wing members having a left indicating indicia and the remaining said wing member having a right indicating indicia where said wing structure can be pivoted relative to said cap permitting alignment of either said left indicating indicia or said right indicating indicia with said first indicia thereby informing the user which nostril of said left nostril or said right nostril was last sprayed; and lineally moving said injector nozzle relative to said cap causing dispensing of a precise quantity of a misting spray from said injector nozzle.

4. The method as defined in claim 3 wherein following the lineally moving step, the following steps occur;

utilizing a removable cover on said injector nozzle that contains second indicia in the form of referencing the days of the week;

pivoting of said cover relative to said injector nozzle until alignment occurs of a day of the week of said second indicia with said first indicia which is also in alignment with either said left indicating indicia or said right indicating indicia; and fixedly mounting of said cover onto said injector nozzle.

5. A medication applicator with incident reminder system usable alternatively between a pair of locations on a human or other animal body, said medication applicator comprising:

a vessel having an internal reservoir adapted to contain a quantity of a medication;

a cap mounted on said vessel, said cap having first indicia, said first indicia indicating which location was last applied with the medication; and a dispensing nozzle mounted on said cap, said injector nozzle being movable relative to said cap between a dispensing position and a non-dispensing position, said dispensing nozzle also being freely pivotally movable on said cap, said dispensing nozzle having a wing structure forming a pair of diametrically spaced apart wing members, applying a downward force toward said vessel against said wing members results in movement of said dispensing nozzle from said non-dispensing position to said dispensing position with some of the medication to be ejected from said dispensing nozzle, first location indicating indicia located on one said wing member, second location indicating indicia located on the remaining said wing member, with said first location indicating indicia being aligned with said first indicia the user is informed that the first location was last applied, with the second location indicating indicia being aligned with said first indicia the user is informed that the second location was last applied.

6. The medication applicator as defined in claim 5 including:

a cover removably connectable with said dispensing nozzle, said cover being pivotable relative to said dispensing nozzle, said cover having second indicia referencing each day of the week, a selected day of the week of said second indicia to be aligned with either said first location indicating indicia or said second location indicating indicia that is aligned with said first indicia thereby informing the user which day of the week the medication applicator was last used.

* * * * *